United States Patent [19]
Pratt et al.

[11] Patent Number: 5,785,965
[45] Date of Patent: Jul. 28, 1998

[54] VEGF GENE TRANSFER INTO ENDOTHELIAL CELLS FOR VASCULAR PROSTHESIS

[75] Inventors: Richard E. Pratt, Palo Alto; Victor J. Dzau, Los Altos Hills, both of Calif.

[73] Assignee: The Board of Trustees of the Leland Stanford Junior Univ., Palo Alto, Calif.

[21] Appl. No.: 647,821

[22] Filed: May 15, 1996

[51] Int. Cl.$^6$ .......................... A01N 63/00; C12N 15/00
[52] U.S. Cl. ................. 424/93.21; 424/93.1; 424/93.2; 435/172.3; 435/325
[58] Field of Search .............................. 600/36; 623/1, 623/11, 12; 435/172.3, 240.2, 320.1, 325; 424/93.21, 93.1, 93.2; 514/44

[56] References Cited

PUBLICATIONS

Shalaby et al., "Failure of Blood–Island Formation and Vasculogenesis in Flk–1–Deficient Mice," Nature (1995), 376:62–69.

Ahlswede and Williams,"Microvascular Endothelial Cell Sodding of 1–mm Expanded Polytetrafluoroethylene Vascular Grafts," Arteriosclerosis and Thrombosis (1994), 14:25–31.

Iizuka et al., "Quantitative RT–PCR Assay Detecting The Transcriptional Induction of Vascular Endothelial Growth Factor Under Hypoxia," Biochemical and Biophysical Research Comm. (1994), 205:1474–1480.

Millauer et al., "High Affinity VEGF Binding and Development Expression Suggest Flk–1 as a Major Regulator of Vasculogenesis and Angiogenesis," Cell (1993), 72:835–846.

Shavani et al., "Optimization of Recombinant t–PA Secretion From Seeded Vascular Grafts," J. of Surgical Res. (1994), 57:495–504.

Barleon et al., "Differential Expression of the Two VEGF Receptors flt and KDR in Placenta and Vascular Endothelial Cells," J. of Cellular Biochemistry (1994), 54:56–66.

Williams et al., "Microvascular Endothelial Cell Sodding of ePTFE Vascular Grafts: Improved Patency and Stability of the Cellular Lining," J. of Biomedical Materials Res. (1994), 28:203–212.

Zhang et al., "Enhancement of Tumor Growth and Vascular Density by Transfection of Vascular Endothelial Cell Growth Factor Into MCF–7 Human Breast Carcinoma Cells," J. of the National Cancer Institute (1995), 87:213–219.

Sackman et al., "Synthetic Vascular Grafts Seeded with Genetically Modified Endothelium in the Dog: Evaluation of the Effect of Seeding Technique and Retroviral Vector on Cell Persistence in vivo," Cell Transplantation (1995), 4:219–235.

Tischer et al., The Human Gene for Vascular Endothelial Growth Factor, The J. of Biological Chemistry (1991), 266:11947–11954.

Zwiebel et al., "High–Level Recombinate Gene Expression in Rabbit Endothelial Cells Transduced by Retroviral Vectors," Science (1989), 243:220–243.

Noishiki et al., "Autocrine Angiogenic Vascular Prosthesis with Bone Marrow Transplantation," Nature Medicine (1996), 2:90–92.

Williams and Jarrell,"Tissue–Engineered Vascular Grafts," Nature Medicine (1996), 2:32–34.

Orkin et al. "Report and Recommendations . . . Gene Therapy" NIH Dec. 7, 1995 pp. 1–40.

Anderson."Gene Therapy," Scientific American Sep. 1995 pp.124–127.

Ledley. Hum Gen Ther 2:77–83 (1991).

von der Leyen et al. P.N.A.S. 92: 1137–1141 (Feb. 95).

Muhlhauser et al. Circulation Res. 77(66) 1077 –1086, (Dec. 1995).

Maglione et al. Oncogene 8(4): 925–31 (Apr. 1993).

*Primary Examiner*—Jasemine C. Chambers
*Assistant Examiner*—Deborah J. R. Clark
*Attorney, Agent, or Firm*—Bozicevic & Reed LLP; Pamela J. Sherwood

[57] ABSTRACT

Endothelial cells derived from subcutaneous adipose tissue are genetically modified to express the endothelial cell-specific angiogenic factor VEGF. The modified cells are sodded onto a vascular prosthesis for transplantation into an autologous or allogeneic recipient. The method accelerates endothelialization on the luminal surface of the vessel, and promotes collateral circulation in distal ischemic organs.

11 Claims, 4 Drawing Sheets

Prolonged Secretion of hVEGF from Sodded Grafts in Culture

VEGF GENE TRANSFER INTO ENDOTHELIAL CELLS FOR VASCULAR PROSTHESIS

This invention was made with government support from the National Institutes of Health. The Government has certain rights in this invention.

INTRODUCTION

1. Field of Invention

The field of this invention is cardiovascular prosthestic devices.

2. Background

Vascular disease affects a large segment of the human population, and is the leading cause of death in the United States. Each year in the U.S., 800,000 individuals survive an acute myocardial infarct, or "heart attack", while another 200,000 do not survive. The continued presence of occluded coronary arteries in the survivors is believed to be a significant health risk. Therefore, treatments have been developed to either bypass the damaged arteries, or to reduce the occlusion by balloon angioplasty. Coronary arterial bypass graft (CABG) is a procedure in which vascular grafts are anastomosed end-to-side to the internal mammary arteries, bypassing atherosclerotically stenosed coronary arteries.

A complication of CABG is stenosis of the graft, where atherosclerotic lesions evolve as a result of vascular smooth muscle migration into the subintimal space, proliferation and the production of abundant extracellular matrix. Experimental studies suggest that changes in the expression of growth factors by vascular or blood borne cells play an important pathogenic role in vascular damage and lesion formation.

Numerous synthetic biomaterials have been developed as vascular substitutes. Studies have demonstrated that selected materials, e.g. Dacron and ePTFE (expanded polytetrafluoroethylene) grafts, can be successfully incorporated in both the large and the small caliber host arteries of animal models. Morphologically, the healing process consists of a series of complex events including fibrin deposition and degradation, monocyte-macrophage recruitment and flow-oriented cell-layer generation, this last event being the complete endothelialization of the arterial substitute. However, the flow surface of synthetic vascular grafts has generally remained unhealed in humans, particularly in the small caliber vessels.

In order to improve the patency of synthetic vascular grafts for human small artery bypass, new strategies have been attempted. Despite major efforts to overcome these problems, however, endothelialization on vascular prosthesis in humans is still extremely delayed. Previous attempts have seeded endothelial cells onto synthetic grafts, but this results in incomplete endothelialization as well as cell denudation upon exposure to flow. This method is also cumbersome, and requires allogeneic endothelial cells or cultured endothelial cells from other strains. Isogeneic cells from autologous jugular vein or saphenous vein may be used, but this approach requires surgical procedures prior to grafting. Other investigators have used cell sodding techniques to resolve the problem of seeding. Unfortunately, this technique is still limited by the slow rate of endothelialization. There is therefore great interest in new methods of improving the endothelialization and graft healing of synthetic vascular grafts in humans.

Relevant Literature

Sackman et al. (1995) *J. Cell Transplant* 4:219–35 evaluates synthetic vascular grafts seeded with autologous endothelial cells transduced with retroviral vectors. While the initial gene transfer was successful, transduced endothelial cells were deficient in their ability to stably adhere and colonize synthetic vascular grafts in vivo. Shayani et al. (1994) *J. Surg. Res.* 57:495–504, reports the seeding of vascular grafts with genetically engineered endothelial cells secreting tissue plasminogen activator. The cells were able to maintain t-PA secretion after exposure to in vitro flow conditions.

Williams et al. (1994) *J. Biomed. Mater. Res.* 28:203–12 evaluate the use of endothelial cell transplantation to accelerate the formation of a cell lining using microvascular endothelial cells derived from canine falciform ligament fat. A cellular lining was found to form on the inner surface of the graft, which was associated with improved graft function. Ahlswede and Williams (1994) *Arterioscler Thromb* 14:25–31 morphologically evaluate the very early events of healing of 1-mm-internal-diameter expanded polytetrafluoroethylene (ePTFE) grafts that were treated with autologous microvessel endothelial cells at the time of graft implantation. The luminal lining of cells exhibited morphological characteristics indicating they were anti-thrombogenic based on morphological criteria, and exhibited characteristics of endothelium. Noishiki et al. (1996) *Nature Med.* 2:90–92 describes the use of porous ePTFE grafts with bone marrow transplantation.

The genetic modification of rabbit aortic endothelial cells with retroviral vectors containing adenosine deaminase (ADA) or rat growth hormone (rGH) genes is shown in Zwiebel et al. (1989) *Science* 243:220–2. Zhang et al. (1995) *J Natl Cancer Inst* 87:213–9 investigates the effect of constitutive expression of VEGF on tumor formation by breast carcinoma cells. Koh et al. (1995) *J. Clin. Invest.* 95:114–121 shows targeted expression of transforming growth factor-beta 1 in intracardiac grafts promotes vascular endothelial cell DNA synthesis. A description of hepatocyte growth factors is found in Miyazawa et al. (1992) *J. Biol. Chem.* 268:10024–10028 and Maher et al. (1993) *J. Clin. Invest.* 91:2244–2252. The angiogenic effect of FGF variants is discussed in Nabel et al. (1993) *Nature* 362:844–846; Brustle et al. (1992) *Oncogene* 7:1177–1183. The in vivo gene transfer of nitric oxide synthase is described in von der Leyen et al. (1995) *P.N.A.S.* 92:1137–1141.

SUMMARY OF THE INVENTION

Synthetic vascular grafts are treated with genetically modified endothelial cells prior to transplantation. The endothelial cells are derived from the microvessels of adipose tissue, and are genetically modified to express a vascular cell growth factor, thereby facilitating rapid endothelialization of the synthetic graft. Expression and secretion of the growth factor from the transfected cells in the graft stimulates angiogenesis in the ischemic tissue downstream from the graft.

DATABASE REFERENCES FOR NUCLEOTIDE AND AMINO ACID SEQUENCES

The Genbank accession number for the complete mRNA sequence of human placental growth factor (PlGF) is X54936, reference: Maglione et al. (1991) *P.N.A.S.* 88:9267–9271. The Genbank accession number for exon 6 of the splice variant PlGF-2 is S57152, reference: Maglione et al. (1993) *Oncogene* 8:925–931.

The mRNA encoding human vascular endothelial growth factor (VEGF) was originally described by Leung et al. (1989) *Science* 246:1306–1309; Genbank accession number M32977. The region of nucleotides 57–134 is the signal peptide, the mature protein is encoded by nucleotides 135–629.

Exons in the splice variants of VEGF have the Genbank accession numbers S85199; S85199 S2; S85199 S3; S85222; and S85224; reference: Houck et al. (1991) *Mol. Endocrinol.* 5:1806–1814. Four splice variants have been described, of 206, 189, 165 and 121 amino acids in length. The 165 aa form is missing exon 6, while the 121 aa form is missing exons 6 and 7.

The amino acid sequence of human transforming growth factor (TGF) β1 has the Swissprot accession number P01137. The amino acid sequence of human basic fibroblast growth factor (bFGF) has the Swissprot accession number P09038; the complete cDNA sequence has the Genbank accession number M27968. The amino acid sequence of human acidic fibroblast growth factor (aFGF) has the Swissprot accession number P05230, P07502.

DESCRIPTION OF THE SPECIFIC EMBODIMENTS

Methods are provided for the preparation of an improved synthetic vascular graft (prosthesis). The prostheses are used as a replacement for natural vessels, e.g. arteries and veins, during vascular bypass or replacement procedures. The thrombogenicity of synthetic materials conventionally used in such prostheses is reduced by the deposition of host or donor endothelial cells in the interstices of the prosthesis interior wall. The growth of such endothelial cells after deposition is increased by genetically modifying the cells to express a vascular growth factor. The genetic modification provides an additional benefit by releasing the vascular growth factor after transplantation, thereby stimulating angiogenesis in the region.

Genetically modified endothelial cells are deposited on a synthetic vessel prior to transplantation. As used herein, "vessel" shall be intended as the acellular synthetic graft, and "prosthesis" shall be intended as the vessel having endothelial cells deposited on the luminal surface. Adipose tissue from an autologous or other suitable donor is used as a source of microvessel endothelial cells. The endothelial cells are genetically modified by the introduction of an expression vector encoding a vascular cell growth factor. The modified endothelial cells may be cultured in vitro after deposition on the prosthesis and prior to transplantation.

The use of endothelial cells isolated from microvessels of adipose tissue is advantageous, because the requisite number of cells can be easily isolated from the graft recipient or a donor prior to the transplantation procedure. Although large vessel and microvascular endothelial cells both provide an anti-thrombogenic blood interface in tissue, these two cell types exhibit distinct morphologies. Microvascular endothelial cells exist as tubes, forming complex tight junctions with themselves and other cells, while large vessel endothelial cells are extremely attenuated squamous cells, often aligned with flow direction and having simple junctional associations.

Adipose tissue is obtained surgically from a suitable donor. Generally the tissue donor will be of the same species as the recipient, e.g. autologous, syngeneic, or allogeneic donors, preferably autologous. It is preferable to use subcutaneous fat, because it contains very few contaminating cell types. Any surgical method as known in the art may be used to obtain the adipose tissue. In a preferred embodiment, the tissue is obtained by suction-assisted lipectomy, a plastic surgical technique used to remove focal fat deposits. A metal cannula with side holes is connected to a high pressure vacuum, removing fat from the face, neck, breasts, abdomen, thighs, etc. The amount of tissue obtained will vary with the length of synthetic vessel to be transplanted. Usually at least about 1 g of fat will be removed, more usually at least about 10 g, and usually not more than about 100 g will be necessary. Additional fat may be removed for cosmetic or other reasons.

Microvessel endothelial cells are isolated from adipose cells present in the tissue. The tissue is mechanically minced or chopped, and treated with an enzyme capable of digesting extracellular matrix proteins, e.g. type I collagenase, dispase-collagenase, etc. The dissociated cells are readily separated into endothelial and adipose fractions based on bouyancy, e.g. centrifugation, density gradients, etc. The isolated endothelial cells may be frozen in liquid nitrogen for future use, or placed into culture medium in vitro and grown in a conventional manner for maintenance or expansion of cell numbers. The endothelial nature of the cells may be confirmed by various assays, for example determining the presence of factor VIII-related antigen, uptake of acetylated low-density lipoprotein, expression of endothelial cell specific markers, and the like.

The endothelial cells are genetically modified to express a vascular growth factor by the introduction of a nucleic acid vector encoding the growth factor, and sequences necessary for its expression. The vector may be episomal, e.g. plasmid or virus, or integrated into the host cell genome. Examples of expression vectors for mammalian cells known in the art and commercially available include plasmids, retrovirus-based vectors (see Zweibel et al., supra.), herpes simplex virus-based vectors (see Mesri et al. (1995) *Circ. Res.* 76:161–167) and adenovirus-based vectors (see Muhlhauser et al. (1995) *Circ. Res.* 77:1077–86). Plasmid vectors may include sequences from SV-40 virus or Epstein Barr virus, such as those that increase the stability of the vector after transfection.

Endothelial cell specific vascular growth factors include VEGF; PlGF; TGF-β1; aFGF and bFGF; and hepatocyte growth factor. The nucleotide sequences of the genes encoding these proteins may be accessed as previously cited. Of particular interest is VEGF, an endothelial cell specific mitogen, which is structurally related to platelet-derived growth factor. Four splice variants have been described, of 206, 189, 165 and 121 amino acids in length. The 165 aa form is missing exon 6, while the 121 aa form is missing exons 6 and 7. Any one of the variants is suitable. The origin of the growth factor will be selected to minimize the antigenicity of the protein, and maximize the activity. Generally the species will be the same, e.g. human genes into humans, mouse into mouse, etc. VEGF is highly conserved, and so has a high degree of cross-species activity.

Additional genes may be co-transfected with the vascular growth factor. The second gene may encode a protein that inhibits the growth of intimal cells, for example, inducible nitric oxide synthase (iNOS) or endothelial cell nitric oxide synthase (ecNOS). Proteins that inhibit thrombosis, e.g. tissue plasminogen activator (tPA), urokinase, and streptokinase, are also of interest for co-transfection. The transfected gene(s) will be present in an expression construct, as described below. The second gene may be present on the same or a separate expression construct from the vascular growth factor gene.

The expression construct is prepared in conventional ways. The sequence of the vascular growth factor open reading frame may be obtained from genomic DNA, cDNA, be synthesized in vitro, or combinations thereof. Where the vector limits the size of insert that can be accomodated, e.g. retrovirus, then cDNA will be preferred. For other vectors, it has been found that introns stabilize the mRNA. Primers or adapters may be added by ligation, polymerase chain reaction, etc. to provide for convenient restriction endonuclease sites.

The vector will include regulatory sequences for the expression of the growth factor in endothelial cells, including a promoter, optional enhancer, termination sequences, and the like. The vascular growth factor is inserted 3' to a promoter, and sequences for initiation of translation, that are operable in mammalian cells. A wide variety of promoters have been described in the literature. They are constitutive or inducible, where induction may be associated with a specific cell type or a specific level of maturation. Of particular interest are constitutive high level promoters, including the β-actin promoter, SV40 early and late promoters, immunoglobulin promoter, human cytomegalovirus promoter, etc., as well as regulatable promoters such as the tetracycline-regulated promoter system or the metallothionine promoter. The promoters may or may not be associated with enhancers, where the enhancers may be naturally associated with the particular promoter or associated with a different promoter.

A termination region is provided 3' to the growth factor coding region, where the termination region may be naturally associated with the cytoplasmic domain or may be derived from a different source. A wide variety of termination regions may be employed without adversely affecting expression.

The various manipulations may be carried out in vitro or may be performed in an appropriate host, e.g. E. coli. After each manipulation, the resulting construct may be cloned, the vector isolated, and the DNA screened or sequenced to ensure the correctness of the construct. The sequence may be screened by restriction analysis, sequencing, or the like.

The endothelial cells are transformed with the expression vector, using any convenient method. Techniques known in the art include calcium phosphate precipitated DNA transformation, electroporation, protoplast fusion and liposome mediated fusion, DNA-coated particles, transfection, and infection, where the chimeric construct is introduced into an appropriate virus.

The growth factor genes may be modified in a variety of ways. Sequence analogs may be prepared by oligopeptide synthesis. The growth factors may be produced as a fusion protein, where another peptide sequence provides for modulation of stability in vivo, localization, and other functional changes. Various peptides may be used, such as the immunoglobulin constant region, e.g. IgG Fc (non-complement binding isotypes), portions of homing receptors, ligands to cell surface receptors, and the like.

The genetically modified endothelial cells are placed onto the surface of a synthetic vessel, where the vessel is a tubular member having a substantially uniform bore. Suitable materials for the vessel include expanded polytetrafluoroethylene (e-PTFE) and dacron. High porosity ePTFE may be used for some purposes, where the slit-like fissures in the vessel well are in the range of 90 μm in size (Noishiki et al. supra.) The vessel will generally be small caliber, usually at least about 0.5 mm in internal diameter, more usually at least about 1 mm in diameter, and not more than about 5 mm in diameter, more usually not more than about 3 mm in diameter. The vessel may be cut into lengths prior to deposition of the endothelial cells, generally ranging from 1 to 25 cm in length. The vessel may be pre-incubated with the media used for cell deposition for a period of from about 0.5 to 3 hours.

The cells are deposited on the vessel by sodding or seeding methods, as known in the art. Sodding procedures place the cells directly onto the polymeric internal surface of the vessel as well as into the interstices of the vessel, generally under mild pressure. For example, one termini of the vessel may be clamped, and the cells injected with a syringe through the open end. The vessel is porous to water, and so the media is forced through the interstices of the wall, while the cells are retained. Usually a psi of at least about 1 will be used for deposition, and usually not more than about 10 psi.

Seeding procedures mix the cells with blood or plasma, and then add to the vessel during the pre-clotting period. There are several versions of the technique known as seeding. The synthetic grafts can be coated with collagen or fibronectin prior to the addition of endothelial cells into the lumen. The synthetic graft is then incubated in vitro with rotation to allow the binding of the endothelial cells to the lumenal surface. After several hours or days culture, the graft can be implanted. Alternatively, autologous blood can be forced under pressure through the interstices of the synthetic graft to allow retention of blood cells and protein onto and into the graft pror to addition of the endothelial cells (either passively are actively under pressure). A third alternative is to mix the endothelial cells with the blood prior to the application onto and into the graft.

The number of cells deposited on the vessel will be at least about $10^4$ cells per $cm^2$ of luminal surface, more usually at least $10^5$ cells/$cm^2$, peferably from about $4-6\times10^5$ cells/$cm^2$, and usually not more than about $10^6$ cells/$cm^2$. The cells are deposited in any convenient sterile medium, e.g. PBS, normal saline, M199, DMEM, and the like. The volume of medium will be sufficient to resuspend the cells, generally ranging from about 1 to 25 ml of medium.

After deposition, the prosthesis may be implanted immediately into the recipient, or maintained in culture for a period of time. The culture conditions are conventional for endothelial cells, for example, the prosthesis may be deposited in a plate or well containing medium and fetal calf serum, then incubated at 37° C. The culturing medium is changed at least every 2–3 days, usually daily. The prosthesis will generally be maintained in culture for not more than about three weeks, usually for not more than about two weeks, and preferably will be used within about one week.

The recipient for the prosthesis may be any mammalian species, including canines; felines; equines; bovines; ovines; etc. and primates, particularly humans. Animal models, particularly small mammals, e.g. murine, lagomorpha, etc. are of interest for experimental investigations. The prosthesis is useful for any vascular bypass or replacement surgery, such as may be used in any situation in which the flow of blood through a vessel has been compromized. This may result from atherosclerosis with lesion formation and intimal hyperplasia or from vascular injury. This would include coronary artery disease, peripheral vascular disease or other forms of occlusive arterial disease. The method of surgical replacement is conventional for synthetic material vascular grafts.

The following examples are offered by way of illustration and not by way of limitation.

EXPERIMENTAL

Materials and Methods

Plasmid Construction: A mammalian expression vector encoding human $VEGF_{165}$ (pcDNAhVEGF) was prepared from pLen-165 (Tischer et al. (1991) *J. Biol. Chem.* 266:11974–54). A Bam HI fragment, containing the sequences for human $VEGF_{165}$, was ligated to the BamHI site of the expression vector pcDNA3 (Invitrogen). Expression from this vector is under the control of a cytomegalovirus (CMV) promoter. The orientation was confirmed by digestion of the resultant plasmid with AflIII. A beta-galactosidase expression vector, pSV-β-Galactosidase (Promega), was used to assess transfection efficiency.

Endothelial Cell Isolation, Culture and Characterization: Rabbit adipose tissue derived cells (RATCs) were isolated from New Zealand White rabbit falciform ligament fat as described by Williams et al. (1994) supra., with some modifications. Briefly, 10–15 g subcutaneous fat was obtained from anesthetized rabbits. The fat was minced with scissors, incubated for 30 min at 37° C. with 8 mg/mL type 1 collagenase (Gibco BRL), and 8 mg/mL bovine serum albumin in Dulbeccco's divalent cation free phosphate buffered saline. The mixture was centrifuged at 700 g for 5 minutes at 4° C. and the pellet was resuspended in PBS, centrifuged again, resuspended in M199 media with 20% fetal calf serum (FCS) and seeded onto 1% gelatin-coated plates. Twenty minutes later the cells were rinsed with PBS to remove red blood cells and unattached cells. Cells were cultured at 37° C. in a humidified, 5% $Co_2$ atmosphere. The cell yields were determined after tripsinization using a Coulter counter and cell viability was determined with trypan blue staining followed by examination on a hemocytometer. The culture medium was changed routinely three times per week and the cells were passaged with 0.05% trypsin-EDTA (Gibco-BRL) and replated on uncoated plastic dishes at split ratio of 1:3. Cells from passages 2 to 9 were used in these experiments.

The cultures were characterized immnunohistochemically using antibodies specific for factor VIII-related antigen (polyclonal, Incstar cat# 81935, 1/3000 dilution), alpha smooth muscle actin (monoclonal, Zymed cat# 08–0053) cytokeratin peptide 18, (monoclonal, Sigma chemical company cat# C-8541) and fibroblast (monoclonal, Dako cat# M877). Secondary antibodies were biotinylated rabbit anti-goat IgG for factor VIII and biotinylated goat antimouse IgG for the others.

Cells were also characterized for the uptake of fluorescent labeled acetylated LDL (Dil-Acetyl-LDL, Biomedical Technologies Inc.) as described in Voyta et al. (1984) *J. Cell Biol.* 99:2034–2040. Mouse brain endothelial cells (bEND 3), rabbit aortic smooth muscle cells, COS 7 cells and Hep G2 cells served as positive or negative controls for the above assays.

Transfection into Endothelial Cells: Cells were plated at $3–4 \times 10^5$ cells/cm² in either 6 well plates or 2 well chamber slides. One day later, media was removed, the cells were rinsed and incubate with a DNA-liposome complexes (1 ug DNA: 12 ul lipofectamine, Gibco-Brl) in 1 ml Opti-MEM. In preliminary experiments, various times and DNA:liposome ratios were tested. Five hours later, 1 ml of M199 with 40% FCS was added and the cells incubated overnight at which time the media was removed and replaced with fresh media.

Endothelial Cell Mitogenicity Assay: to prove the secreted hVEGF protein was biologically active, a mitogenic activity assay was performed on human umbilical cord vein endothelial cells (HUVEC, ATCC# CRL-1730) as described in Breier et al. (1992) *Development* 114:521–532, with some modifications. Subconfluent RATCs were transfected with pcDNAhVEGF vector or control β-Gal vector as described above. After 2 days incubation, the media were removed and replaced with serum-free media. Serum-free conditioned medium was collected, diluted as indicated in figure legends and added to the test HUVECs. The test cells had been seeded at same time in Dulbeccco's modified Eagle's media (DMEM)/F12 with 10% FCS at the density of $2 \times 10^4$ cells/6 well plate. Prior to incubation with HUVECs, the conditioned media was mixed with 1 ug monoclonal anti-human VEGF neutralizing antibody (R&D System) or vehicle. Five days later, cells were dissociated by exposure to trypsin-EDTA and counted in a Coulter counter. Values are means ± SD of triplicate wells.

VEGF Direct ELISA: ELISA were performed on ninety-six well microtiter plates as described in Koch et al. (1994) *J. Immunol.* 152:4149–56. Standard curves were generated by coating the wells with human recombinant $VEGF_{165}$ (0.31–≦2 ng/100 ul, R&D System) diluted in Tris-buffered saline (TBS). VEGF levels in fresh culture media and conditioned media was determined by diluting samples with TBS. Wells containing the samples or standards were incubated at room temperature over night. Non specific sites were then blocked with 3% BSA, 0.05% Tween-20 in TBS for 1 hour at 37° C. A mouse monoclonal anti human $VEGF_{165}$ antibody (1.0 ug/ml, R&D System) was added and incubated at 37° C. for 1 hour. Plates were then washed five times with 0.05% Tween-20 in TBS and then incubated with biotinylated goat antimouse IgG antibody (0.5 ug/ml, American Qualex) for 30 min at 37° C. Plates were again washed five times with 0.05% Tween-20 in TBS, avidin-alkaline phosphatase (1 ug/ml, American Qualex) was added and incubated for 30 min at 37° C. Plates were again washed five times with 0.05% Tween-20 in TBS and then substrate solution (O-nitrophenylphoshate diluted in diethanolamine buffer, 1 mg/ml, Bio-Rad) was added. The reaction was stopped by adding 0.4 N NaOH and the absorbance at 405 nm was determined on a microplate auto reader (Model EL310; Bio-Tek instruments). A standard curve was generated by plotting absorbance vs known hVEGF concentrations. The limit of sensitivity of the assay was 3.1 ng/ml.

PCR Detection of VEGF Expression: Confluent RATCs in T25 culture plates were harvested every 3 days up to 22 days after transfection by placing the cell in 1 ml of $RNA^{Zol}$ TM B (Tel-Test). Total RNA was extracted following the manufacturer's protocol. CDNA synthesis was carried out in 20 ul of PCR buffer with 1 ug of total RNA and MMLV reverse transcriptase (Gibco-BRL), in the presence of dNTPs, RNAase Inhibitor, and random hexamers for 60 minutes at 42° C. followed by 10 minutes at 99° C. PCR was performed with a sense primer [SEQ ID NO:1] corresponding to the T7 promoter in the expression vector (5'-TMTACGACTCACTATAGGG-3') and an anti-sense primer [SEQ ID NO:2] corresponding to nucleotides 491–512 of VEGF-165 (5'-TTTTTGCAGGAACATTTACACG-3') plus Tag DNA polymerase (Gibco-BRL). The PCR reaction was carried out for 35 cycles (1 minute at 94° C., 1 minute at 57° C. and 1 minute at 72° C.) plus 1 cycle of 15 minutes at 72° C. Following the PCR, amplification products (557 bp) were analyzed by agarose gel electrophoresis and detected with ethidium bromide.

Cell Sodding onto Vascular Prosthesis and Hybrid Organ Culture: he ePTFE grafts (3 mm internal diameter), supplied by the W. L. Gore Company, were standard clinical quality grafts. Five centimeter segment of ePTFE graft was clamped at one end with hemostatic forceps and connected at the other end to a T connector and placed in a glass tube. Sodding media was injected 1 hour into the lumen of the graft using a 10 ml syringe 30–60 min. prior to sodding. A T-connector was positioned between the graft and the syringe. Approximately 10 ml sodding media was injected into the lumen and through the interstices of the graft. The graft was then incubated at room temperature. Sodding media was then removed and replaced with a suspension of transfected cells, 1 day after transfection, and mixed with 200 µl heparin. The graft was again pressurized using a 10 syringe filled with sodding medium. A total of 5 ml of medium was pushed through the graft to ensure that almost all cells were filtered into the graft surface. The fluid which passed through the graft was evaluated and found to be devoid of cells. The initial cell numbers sodded into luminal surfaces of the graft were 4–6×10$^5$/cm$^2$. Control grafts were treated with pSV-β-Galactosidase control vector transfected cells in the same way.

The sodded grafts were cut into 1.5 cm length and incubated in 24 well plates with 1 ml Medium 199 with or without 20% FCS. The media were changed every day. Serum-free conditioned medium were collected for a 24 hour period every 3 days. This serum-free conditioned media was assayed for VEGF using both the direct ELISA and mitogenic bioassays described above.

Time 0.7 days, 10 days, 14 days, 21 days after cell sodding, the grafts were also analyzed for β-gal expression, presence of endothelial cells and for total cell coverage. The grafts were fixed with 0.25% glutaraldehyde and stained with X-gal solution for 1 hour at 37° C. to detect β-Gal expression and then stained with the nuclear specific stain bis-benzimide trihydrochloride (Hoechst dye No. 33342) to asses total cell number. The grafts were also incubate with 50 ul of acetyl Dil LDL for 4 hours to detect endothelial cell and then fixed with 3% formalin and then immediately examined under UV lamp.

To semi-quantify cell coverage, 5 random pictures were taken of each graft at 100 X magnification. The area of positive Hoechst dye staining and total area was measured and the % area covered was calculated.

Implantation of ePTFE grafts sodded with Transfected Cells: Thirty nine rabbits were used for grafts implantation; VEGF 13, β-Gal 13, control grafts without cells, 13. The sodded grafts were prepared as described above using cells 2 days following transfection. For acute experiment (8 hours observation) the cultured cells were used to analysis cell retention and expression of VEGF or β-Gal. For chronic experiment (14, 28 days observation) autologous RATCs which were isolated from each rabbit 7–14 days prior to transfection. The transfections were performed in T 75 flasks as described above. Two days after transfection (15 minutes prior to the operation), the RATCs were dislodged from the flask using trypsin-EDTA and resuspended in 5 ml PBS containing 20% autologous rabbit serum collected at the time of adipose tissue harvest.

General anesthesia were induced in 2.7–4.0 kg New Zealand White rabbits via intramuscular injections of xylazine (5 mg/kg), ketamine hydrochloride (40 mg/kg) and atropine (0.04 mg/kg). The rabbits were intubated and maintained with halothane inhalation under spontaneous respiration. The entire surgical procedure was undertaken under strict sterile conditions using aseptic techniques. A midline abdominal incision was made and the infrarenal aorta was exposed. A 1.5 centimeter segment of aorta distal renal artery and proximal to its bifurcation was ligated, and the aorta was clamped proximally and distally and divided after injection of heparin 30 U/kg systemically. The sodded and non-sodded ePTFE grafts (3 mm internal diameter, 2.2–3.0 cm in length) were anastomosed in an end to end fashion to the aorta using an interrupted 7-0 Gore-Tex suture. During suturing, the graft was kept moist with saline solution to avoid desication. After establishing meticulous homeostasis, the retroperitoneum and the abdominal wall were closed in layers. During surgery the animals were allowed to cool (oral temperature decreased to 33° C.) in order to protect the spinal cord from ischemic injury. Following surgery, the animals were transferred to the animal ICU and were actively warmed to normal body temperature.

All grafts were retrieved on a predetermined postoperative schedule (8 hours, 14 days, and 28 days, each group; n=4–5). At graft retrieval, laparotomy incisions were made and the grafts were explanted following addition of heparin to avoid thrombus formation. The explanted grafts were rinsed with PBS 3 times and fixed with 3% formaldehyde solution or 0.25% glutaralaldehyde solution.

Analysis of graft. In acute experiments the grafts were observed macroscopically to detect thrombus formation. The graft were stained with X-gal solution for 60 min at 37° C. to observe β-galactosicidase expression. In chronic experiments the samples were cut into 6 µm thickness sections with cryostat (B.H. model TOF) for H.E. staining and immunohistochemical analysis of factor VIII as described above to detect endothelial cells. For the Scanning Electron Microscopy (SEM) the grafts were fixed in phosphate buffer containing glutaraldehyde and paraformaldehyde, washed in 0.1 M phosphate buffer and post-fixed and stained in 1% osmium-tetroxide for 1–2 hours. The grafts were then washed 3 times in distilled water to remove excess phosphate, (thereby avoiding precipitation of uranyl acetate in the following step), stained for 0.5 to 1 hour in 1% aqueous uranyl acetate and washed 3 times in distilled water. The grafts were then step-dehydrated for 15 min each in 30, 50, 70 and 90% ethanol followed by two 10 min soaks in 100% ethanol. The samples were incubate with 100% ethanol with increasing strength of hexamethyl disilazane (HMDS) and then coated with 15 nm gold using Polar SEM coating system and a Polar film thickness monitor (E5500) for determining density of gold. The samples were observed with Philips 505 SEM.

Results RATCs were isolated from explanted rabbit adipose tissues by modification of previously reported techniques and characterized by a combination of immunohistochemical and cytochemical techniques. Approximately 80% of the cultured cells exhibited positive signal following exposed to Dil-Ac-LDL. As controls, mouse brain microvascular cells (bEND 3), a clonal endothelial cell line, displayed 100% positive staining, whereas rabbit aortic smooth muscle cell were uniformly negative. Immunohistochemical staining with an antibody to human Factor VIII RAg was partially positive, with a variable number of cells displaying granular cytoplasmic staining. The pattern and variability are consistent with previous reports in which antibodies raised against human factor VIII RAg was used to characterized culture ECs from rabbit (Conte et al. (1994) *Circulation* 89:2161–2169). Staining for muscle actin showed that less than 0.1% of cells in the cultures exhibited positive immunoreactivity for smooth muscle actin, whereas more than 99% of rabbit aortic vascular smooth muscle cells stained with the appropriate pattern. Staining for cytokeratin 18, a marker of methothelial and fibroblast cells, was also negative in RATCs, while appropriate positive control cells exhibited intense immunoreactivity. Thus, by the criteria employed, the rabbit adipose tissue cells are highly enriched for endothelial cells.

RATCs exhibited a high transfection efficiency following exposure to lipofectamine/DNA complex. Two days following transfection with the β-Gal expression vector, approximately 50% of the cells exhibited positive staining with X-gal. In contrast, neither control (untransfected) cells nor cells transfected with a control vector exhibited positive staining. Cells transfected with the VEGF expression vector exhibited a similar transfection efficiency. However RATCs transfected with β-Gal expression vector were negative.

Figure 1A:
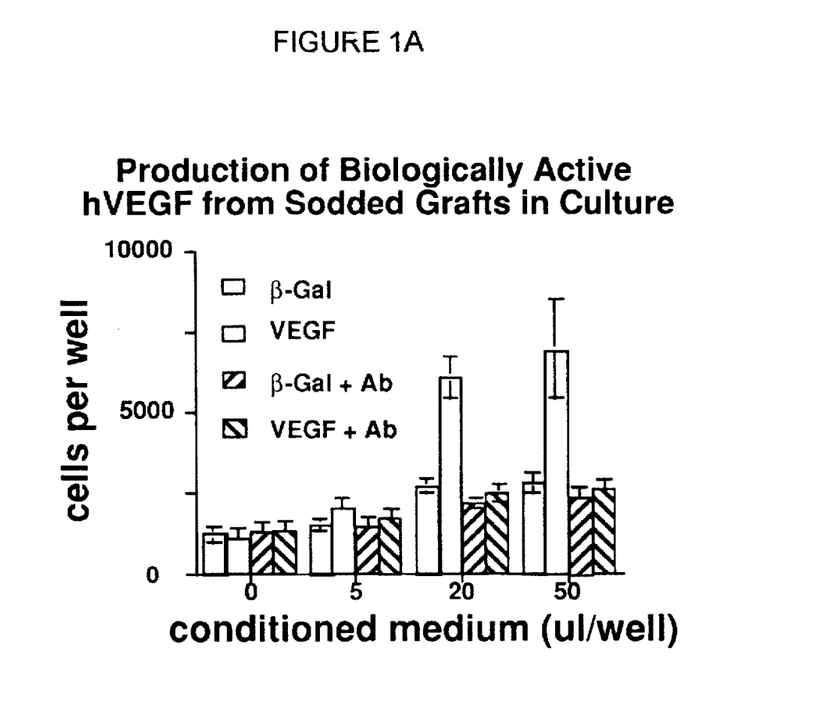
FIG. 1A is a bar graph showing secreted VEGF activity from sodded grafts.

The cell culture supernatants were then assayed for mitogenic activity using HUVEC. The conditioned media collected from cells transfected with the VEGF expression vector induced 3 fold increase proliferation of the HUVEC. The data is shown in FIG. 1A. Following sodding, the grafts were rinsed and incubated for 24 hours in serum free media. The conditioned media was collected and assayed for VEGF in a biological assay using HUVEC as the test cell. The HUVEC were seeded in the presence of DMEM/F12 with 10% FCS in 12 well plates at the density of $1 \times 10^4$ cells/well. The HUVECs were fed 1 ml of fresh serum free media supplimented with 0, 5, 20, or 50 uL of the conditioned media from the grafts. Some of the wells also received 1 μg monoclonal mouse anti-human VEGF neutralizing antibody. The media was replaced every 2 days for 5 days and then the cell numbers were counted in a Coulter counter. Values are mean ± SE of triplicate samples. This mitogenic activity was blocked with a neutralizing monoclonal antibody raised against human $VEGF_{165}$. Media from control group had no significant mitogenic effect.

The time dependence of the expression of hVEGF was then examined. Cells transfected with the VEGF or β-Gal expression vectors were maintained at confluence in T25 flasks. At various times, RNA was harvested from the flasks and analyzed by RT-PCR using primers specific for the transfected $hVEGF_{165}$. The results demonstrate the presence of VEGF mRNA in the transfected cells. The expression was persistent, being detectable as late as 22 days following transfection. No signal was obtained from mRNA isolated from non-transfected cells nor RNA from cells transfected with either the β-Gal expression vector or the VEGF parental vector, pcDNA3. Moreover no signal seen in the absence of RNA nor in RNA samples previously treated with RNAase demonstrating that the product was due to amplification of mRNA and not due to contaminating vector DNA.

In Vitro RATCs Sodding into the Graft and Hybrid Organ Culture. The ability of the transfected cells to be sodded into the vascular grafts was examined. Immediately after sodding with cells transfected with pSV-β-Galactosidase, the grafts were fixed, and stained with the Hoechst dye and X-Gal. At low power, the X-Gal stained grafts were intensely blue. At higher power observation, both X-Gal staining and Hoechst dye staining demonstrated that the RATCs were uniformly sodded into the graft. Over time, the intensity of X-gal staining decreased but was still evident 3 weeks after cell sodding. Dual staining revealed that at 3 weeks, the blue X-Gal staining was cell associated.

Figure 1B:
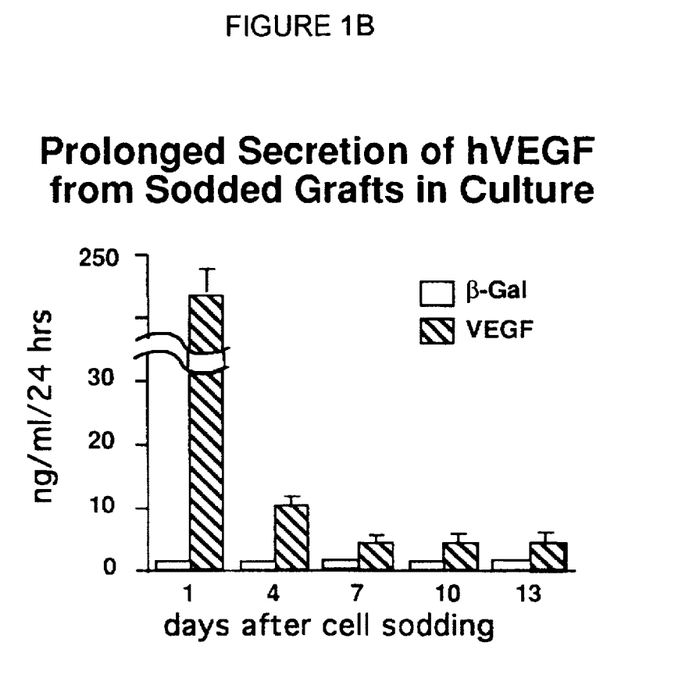
FIG. 1B shows the time course of VEGF secretion from sodded grafts.

The grafts sodded with RATCs transfected with the VEGF expression vector produced biological active $VEGF_{165}$. Following sodding, the segments of graft were incubated for 24 hours in serum-free media. Media was collected and assayed for biological activity using HUVEC cells as the test cell line. Media from grafts lined with cells transfected with the VEGF expression but not grafts lined with the β-Gal expression vector stimulated the growth of HUVEC cells in a dose dependent manner. This growth induction could be abolished by prior incubation of the media with a monoclonal antibody specific for hVEGF. This expression of VEGF was persistent. FIG. 1B shows the time course for VEGF expression in sodded grafts. To assay for VEGF, the media was replaced with serum free media and collected 24 hours later (at the times indicated on the figure. A direct ELISA was performed with the mouse monoclonal anti-hVEGF using recombinant human $VEGF_{165}$ as a standard (0.31–2 ng/100 ul). The limit of sensitivity of the assay was 3.1 ng/ml. hVEGF was detected as early as 24 hours (day 1) posttransfection, and secretion continued for up to 14 days. As anticipated, the greatest release of VEGF, as measured by ELISA, was observed during first day post sodding. However, VEGF could be detected in conditioned media as collected during the 24 hours preceding day 13 post sodding. The level in the conditioned media during this time was 4.4 ng/ml secreted over the previous 24 hour period. No VEGF was detected in the conditioned media from grafts sodded with β-Gal transfected cells.

Since the level of VEGF in the media was above the $ED_{50}$ for VEGF action on endothelial cells, we examined the effects of transfection with the VEGF expression vector on growth of cells on the luminal portion of the graft in organ culture. Seven days following sodding with transfected cells, no difference in cell coverage was observed. After this point, the total coverage in the grafts sodded with the β-Gal transfected cells decreased while the coverage in grafts sodded with cells transfected with pcDNAhVEGF continued to increase up to a maximum value of 80% coverage of the lumen at 21 days. These lumenal cells were endothelial-like, since they took up acetyl Dil LDL. Only scattered areas of positive acetyl Dil LDL uptake were observed in grafts sodded with cells transfected with the p-SV-β-Gal vector.

Figure 2:
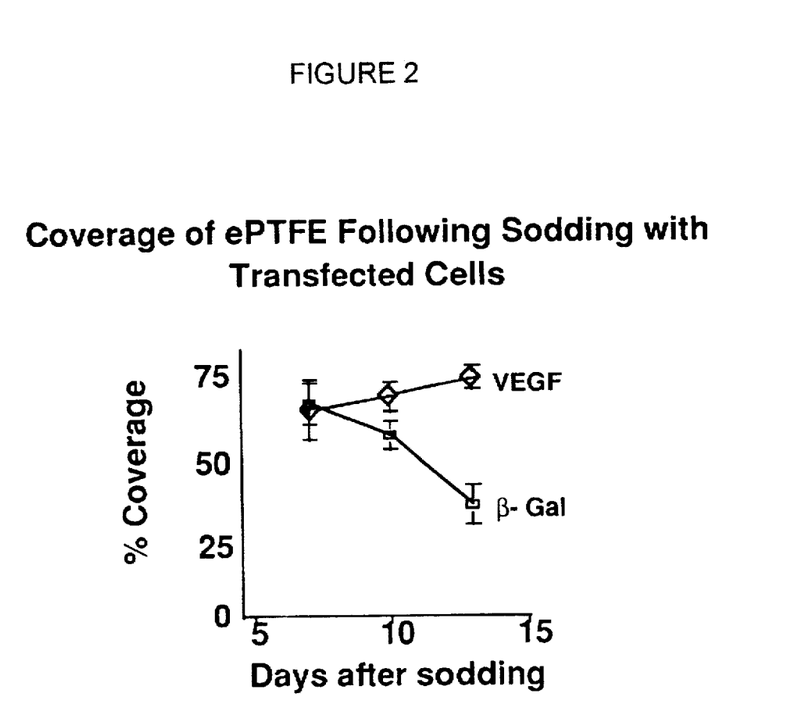
FIG. 2 is a graph showing the rate of endothelialization of ePTFE grafts.

The rate of endothelialization is shown in FIG. 2. Following sodding, the grafts were rinsed and incubated in serum containing media. At various times, the grafts were removed from the wells, stained with H33342 and examined under fluorescent microscopy. The total luminal area and the area of cell coverage was measured and expressed as the percentage of total luminal area.

Graft implantation and removal. Grafts were implanted into the rabbit abdominal aortae for acute and chronic experiments. The mean ischemic time during graft implantation was 32 minutes. After declamping, the sodded graft turned red, however there was no bleeding through the wall of either the sodded or unsodded grafts. Bleeding at the anastomotic sites stopped within 5 minutes. The use of passive hypothermia prevented poliomyelomalacia due to ischemic injury, and all animals with one exception (that received a nonsodding graft) looked healthy during the recovery period. Animal were sacrificed at 8 hours, 14 days, and 28 days after graft implantation to explant the grafts. There was no unusual adhesion, hematoma or seroma formation around the grafts.

Macroscopic analysis. The grafts from all three groups were patent. In acute experiments, no macro thrombi were observed on the luminal surface of the grafts. Compared to non-sodded standard graft, the sodded grafts appeared slightly red due to cell infiltration into the interstices. X-Gal staining of the grafts sodded with β-Gal transfected cells revealed many scattered dark blue areas of staining on the luminal surface. No blue staining was observed on the grafts sodded with the VEGF transfected cells. These results indicate that sodded cells remained in the interstices of the graft wall following eight hours exposure to blood flow.

In the two week chronic experiments, the grafts sodded with the VEGF transfected cells exhibited several white colony patches on the luminal surface. This patchy appearance was observed in mid portion of the graft as well as near the anastomotic sites. At four weeks, the grafts sodded with cells transfected with the VEGF expression vestor exhibited this white color along the entire luminal surface. No fresh thrombus was observed. The β-Gal graft and control non-sodded graft were pink in color at Day 28.

Figure 3:
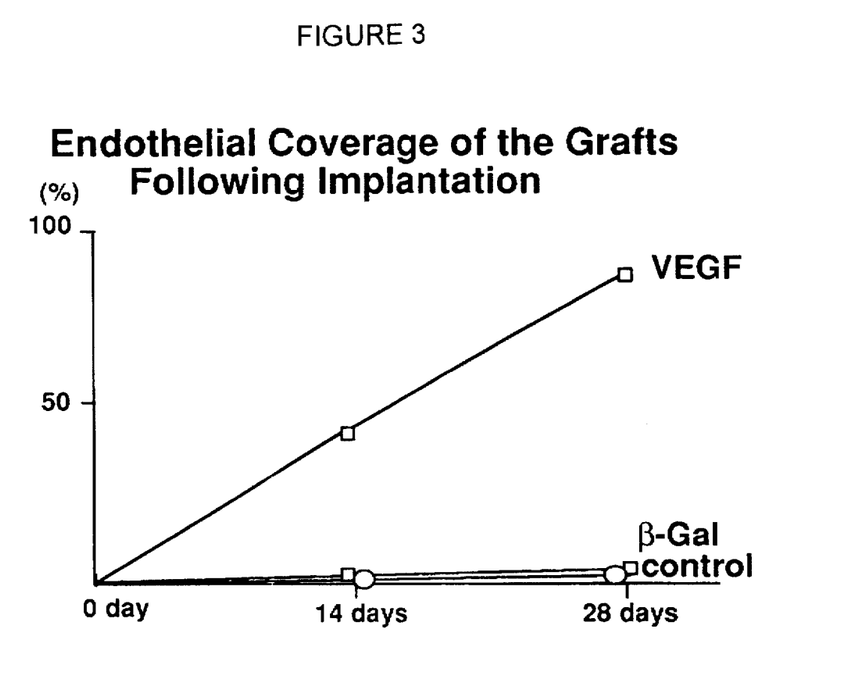
FIG. 3 is a graph showing the endothelial coverage of grafts following implantation in vivo.

Microscopic analysis. The white patches in grafts sodded with the VEGF transfected cells were shown to be endothelial-like cells based on positive Factor VIII-related antigen staining. The regions of the graft removed at two weeks which macroscopically appeared red were shown to have thrombus formation. At 4 weeks, the luminal surface of the grafts were completely lined with a continuous layer of endothelial-like cells, with only a thin neointima formation present. These endothelial-like cells exhibited positive immunoreactivity for factor VIII related antigen. The scanning electron microscopy revealed that the surface had a cobble stone appearance with no evidence of thrombus. On the other hand, grafts sodded with cells transfected with the β-Gal expression vector, observed at 2 weeks and 4 weeks did not exhibit endothelial-like cell lining. Control, unsodded grafts exhibited a fibrin layer on the luminal surface. The endothelial coverage of grafts following implantation in vivo is shown in FIG. 3.

We have demonstrated that RATCs were efficiently transfected with DNA-liposome complex and successfully sodded into synthetic vascular grafts and maintained in hybrid organ culture, continued to secret biologically active VEGF protein into culture media for up to 2 weeks in vitro in these studies. Furthermore luminal surfaces of the graft were covered with endothelial cell lining without intimal thickning in hVEGF transduced grafts at 4 weeks after implantation.

In small-diameter vessels, grafts requires strong antithrombogenic properties to remain patent. Even when treated with high- dose anticoagulants, small-diameter grafts without antithrombogenic properties will occlude. The natural antithrombogenicity of endothelial cells is most reliable for long-term graft patency, and rapid endothelialization is important for the long-term survival of small-caliber vascular grafts. However, endothelialization on vascular prosthesis in humans is extremely delayed. Most clinical vascular grafts do not endothelialize except at the anastomoses, and even this limited endothelialization is very slow.

Previous attempts have seeded endothelial cells onto synthetic grafts, but this results in incomplete endothelialization as well as cell denudation upon exposure to flow. Also, this method is cumbersome and requires allogeneic endothelial cells or isogeneic cells from autologous external jugular vein or saphenous vein.

The subject methods use mixed cultured cells from the subcutaneous fat, which contains high amount of microvascular endothelial cells. Investigators demonstrated that rapid endothelialization requires exogenous or endogenous growth factors that induce endothelial proliferation. VEGF is an endothelial cell-specific mitogen, which accelerates reendothelialization and attenuates intimal hyperplasia in injured rabbit artery. It is shown above that VEGF gene overexpression selectively promotes endothelialization of the prosthetic vascular graft surface and graft healing. VEGF overexpression in endothelial cells may also stimulate proliferation and migration in an autocrine manner.

It is evident from the above results that the subject invention provides for an improvement in the endothelialization of synthetic vascular grafts by the genetic modification of endothelial cells from subcutaneous adipose tissue. Gene therapy overcomes the difficulties around the patency of small caliber vascular prosthesis, providing improved prosthesis that are resistant to failure and enhance collateral circulation in distal ischemic organs.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A vascular prosthesis, comprising:
a synthetic small caliber vessel; wherein deposited on the luminal surface of said vessel are microvessel endothelial cells isolated from subcutaneous adipose tissue and genetically modified by the introduction of DNA encoding human vascular endothelial growth factor (VEGF); operably linked to regulatory sequences for the expression of said VEGF in an endothelial cell.

2. A vascular prosthesis according to claim 1, wherein said VEGF is a splice variany of 165 amino acids in length.

3. A vascular prosthesis according to claim 1, wherein said synthetic small caliber vessel is expanded polytetrafluoroethylene (ePTFE).

4. A vascular prosthesis according to claim 3, wherein said synthetic small caliber vessel is from 1 to 3 mm in internal diameter.

5. A vascular prosthesis, comprising:
an e-PTFE small caliber vessel of 1–3 mm in internal diameter; wherein deposited on the luminal surface of said vessel are endothelial cells isolated from subcutaneous adipose tissue, and genetically modified by the introduction of a plasmid comprising DNA encoding human vascular endothelial growth factor (VEGF) operably linked to regulatory sequences for the expression of said VEGF in an endothelial cell, thereby facilitating rapid endothelialization and reducing the rate of thrombogenicity when compared to conventional synthetic grafts.

6. A method of preparing a vascular prosthesis, the method comprising:
modifying microvessel endothelial cells isolated from adipose tissue by the introduction of a vascular growth factor expression vector encoding human vascular endothelial growth factor (VEGF); operably linked to regulatory sequences for the expression of said VEGF in an endothelial cell;
depositing said modified endothelial cells on the luminal surface of a synthetic small caliber vessel;
wherein said modified endothelial cells express said VEGF, thereby facilitating rapid endothelialization and reducing the rate of thrombogenicity when compared to conventional synthetic grafts.

7. A method according to claim 6, further comprising the step of culturing said prosthesis in vitro for at least about one week following said depositing step.

8. The method according to claim 6, wherein said VEGF is a splice variant of 165 amino acids in length.

9. The method according to claim 6, wherein said adipose tissue is subcutaneous adipose tissue.

10. The method according to claim 6, wherein said synthetic small caliber vessel is expanded polytetrafluoroethylene (ePTFE).

11. The method according to claim 10, wherein said synthetic small caliber vessel is from 1 to 3 mm in internal diameter.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: Other     ( x i ) SEQUENCE DESCRIPTION: SEQ ID NO:1:

TAATACGACT CACTATAGGG                         2 0

( 2 ) INFORMATION FOR SEQ ID NO:2:

( i ) SEQUENCE CHARACTERISTICS:
        ( A ) LENGTH: 22 base pairs
        ( B ) TYPE: nucleic acid

```
        ( C ) STRANDEDNESS: single
        ( D ) TOPOLOGY: linear ( i i ) MOLECULE TYPE: Other ( x i ) SEQUENCE DESCRIPTION: SEQ ID NO:2:

TTTTGCAGG  AACATTTACA  CG                                                22
```